United States Patent [19]

Friedman

[11] Patent Number: 5,220,827
[45] Date of Patent: Jun. 22, 1993

[54] METHOD FOR TESTING THE HARDNESS OF A DENTAL COMPOSITE MATERIAL

[76] Inventor: Joshua Friedman, 11 Blvd. Dr., #2, Danbury, Conn. 06810

[21] Appl. No.: 880,371

[22] Filed: Nov. 21, 1991

Related U.S. Application Data

[63] Continuation of Ser. No. 646,280, Jan. 28, 1991, abandoned.

[51] Int. Cl.[5] .............................................. G01N 3/48
[52] U.S. Cl. ...................................................... 73/81
[58] Field of Search ........................ 73/78, 79, 81–83, 73/866

[56] References Cited

U.S. PATENT DOCUMENTS 4,503,169  3/1985  Randklev ...................... 433/222.1

FOREIGN PATENT DOCUMENTS 1032359   7/1983  U.S.S.R. ................................. 73/78
1267235  10/1986  U.S.S.R. ................................. 73/78

Primary Examiner—Robert Raevis
Attorney, Agent, or Firm—Eugene Lieberstein

[57] ABSTRACT

A device and method for testing the hardness of a dental restorative material before use. The device is a preformed body with an opening in which uncured restorative material is placed for curing under a standard source of light energy for a normal exposure period. The body has a known hardness which is compared against the hardness of the material on the distal side of the body relative to the source of light.

1 Claim, 1 Drawing Sheet

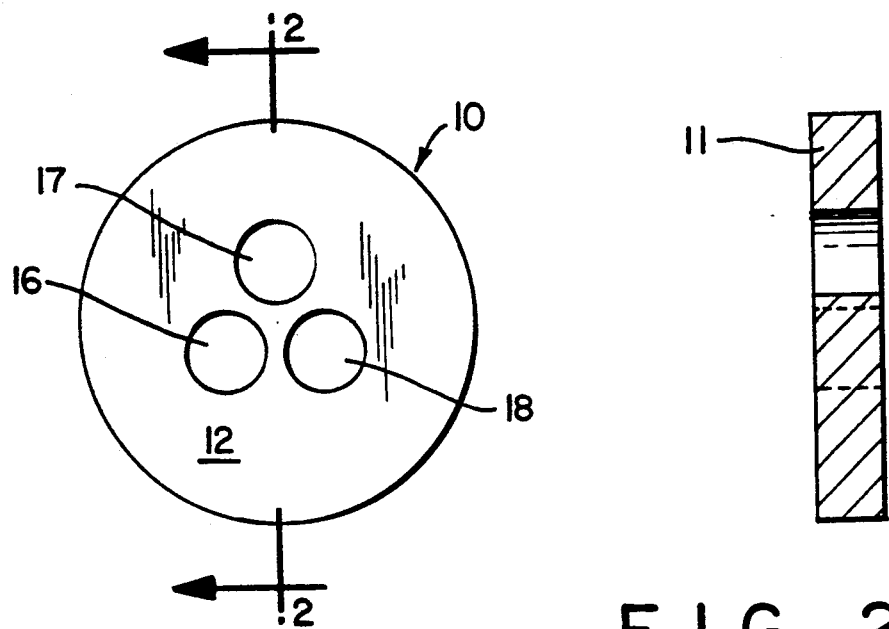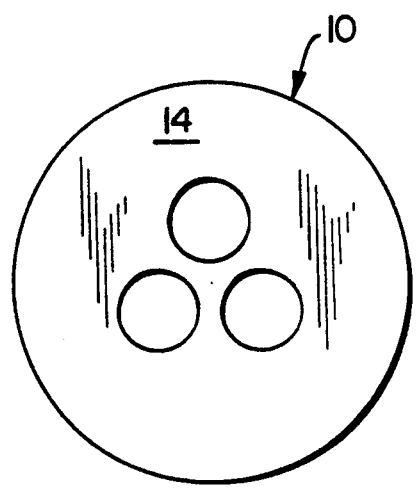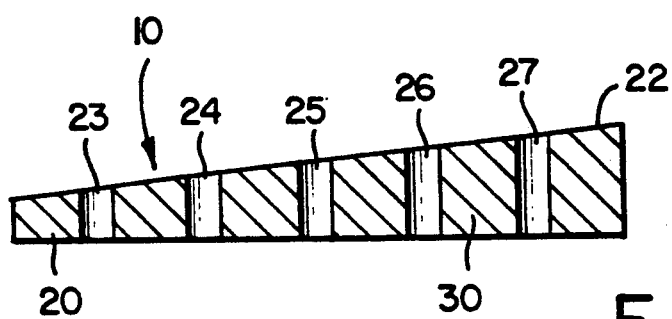

METHOD FOR TESTING THE HARDNESS OF A DENTAL COMPOSITE MATERIAL

This application is a continuation of prior U.S. application Ser. No. 646,280 filed Jan. 28, 1991, now abandoned.

FIELD OF THE INVENTION

This invention relates to a disposable dental material hardness testing device and method to enable a dentist or dental practitioner to determine quickly if a dental restorative material is usable for use in a dental restorative procedure.

BACKGROUND OF THE INVENTION

Dental restorative materials which are cured by exposure to light must possess certain physical and chemical characteristics to be suitable for use by a dentist in filling, restoring or repairing teeth. Dental restorative or composite photocurable materials which are used for filling and repairing teeth should be distinguished from dental compositions used as a bonding agent or to form a glaze or thin coating. In the latter case, the compositions are substantially "unfilled" and of relatively low viscosity, whereas dental restorative materials for filling and restoring teeth are viscous materials containing a substantial concentration of inorganic particulate filler to provide a high viscosity. The photocurable resinous component(s) in the restorative material is homogeneously distributed throughout the composition and must receive sufficient light energy to cause the material to cure uniformly from the top to the bottom of the restoration. There are a substantial number of commercially available curing lamps in the marketplace, all having different light-generating characteristics within the light energy spectrum corresponding to the material to be cured. Moreover, commercially available dental restorative materials come in various shades with different fillers. They have different aging and shelf-life characteristics and tend to degrade in performance or deteriorate at varying temperature levels above ambient.

Accordingly, there is a concern by the dental practitioner as to whether a given restorative material, which the dentist currently has in stock, will, upon the application of light energy, harden throughout the restoration in a reasonable time frame. Currently there is no convenient way for a dentist to be assured that the restorative material available in the dental office has not aged or deteriorated, such that it will not cure properly under the curing lamp or, alternatively, if the curing lamp is capable of curing the material in the time frame specified by the material manufacturer. This is particularly the case for deep posterior restorations which require more light energy and time to effect a cure at the bottom of the restoration. Otherwise, the bottom of the restoration will remain uncured or only partially cured. An uncured or only partially cured restoration does not have the requisite hardness to serve as a dental restoration. This problem comes about because the curing light cures the material from the top down, i.e., the outside proximal surface hardens first, with the lower distal surface furthermost removed from the source of the curing energy curing last. Extensive research has clearly shown that the degree of hardness of a dental restorative material is directly related to its degree of cure. If the restorative material in the area adjacent the pulp chamber base of a tooth cavity is not cured properly, the overall restoration will be physically weak and micro-leakage may occur, as well as patient sensitivity due to the presence of uncured materials which also serves as an irritant to the dental pulp.

SUMMARY OF THE INVENTION

The device and method of the present invention uses a simple, inexpensive, and disposable test indicator for testing a restorative material to determine if the energy output of a curing source of light from any conventional lamp is capable of hardening the bottom layer of restorative material at the distal end nearest the pulp chamber under a normal exposure time frame and, conversely, permit a quick test to determine if the material itself has cured properly or is otherwise defective. Restorative materials may become defective due to aging, exposure to high temperature, or from a manufacturing defect.

The testing device of the subject invention comprises a preformed body composed of a material of known hardness for comparison against the hardness of a dental composite after exposure to light energy, with said body having at least one planar surface on one side of said body and at least one opening extending through the body from each opposite side thereof, with said opening being filled with said composite dental material prior to curing, such that the hardness of said cured dental composite material in said opening, on each opposite side of said body, may be tested by comparison against the hardness of said surrounding body contiguous to said surface.

The method of the present invention for testing the hardness of a conventional uncured dental composite material following exposure to light energy for effecting a cure comprises the steps of: filling a sample of said uncured dental composite into an opening provided in a body composed of a material of known hardness, exposing said filled sample of uncured dental composite from only one side of said body to light energy from a source of curing light over a predetermined time frame of standard duration for effecting a cure, and comparing the hardness of said sample against the hardness of said surrounding body, on at least the side of said body opposite the side which was exposed to light energy. The hardness of the cured sample on the test (bottom) side of the body may be determined by scraping its surface with an instrument, such as a discoid tungsten carbide carver, which is compared to the surrounding surface carvability.

DESCRIPTION OF THE DRAWINGS

Other advantages and objects of the present invention will become apparent from reading the detailed description in conjunction with the accompanying drawings of which:

FIG. 1 is a top view of the preferred hardness testing device of the present invention;

FIG. 2 is a side view in elevation of the device of FIG. 1, taken along the lines 2—2 thereof;

FIG. 3 is a bottom view of the device of FIG. 1; and

FIG. 4 is a cross-sectional view of an alternate embodiment of the testing device of the present invention.

DETAILED DESCRIPTION OF THE INVENTION

The preferred embodiment of the testing device (10) of the present invention is shown in FIGS. 1-3, having a preformed body (11), preferably of disk-like geometry, with a top planar surface (12), a bottom planar surface (14), and a plurality of openings (16), (17), and (18), respectively. The openings (16), (17), and (18) extend through the body of the device (10), from the planar surface (12) to the planar surface (14). The body (11) may be of any desired thickness, preferably from one to eight millimeters, corresponding to the range of normal thickness used in dental restorations in the oral cavity and may be of a desired diameter, such as, for example, one to inches. The body (11) of the device (10) is composed of a material of any desired composition, preferably a polymeric material, having a known hardness, with a barcol hardness range of between 60 and 100. The low end of the hardness range corresponds to microfill materials, whereas the high end of the range corresponds to hybrid filled materials. The preferred polymeric material is an injection-molded, thermosetting material, such as, for example, a polyester glass compound available from Premix Inc., USA.

The hardness disk testing device (10) should possess a hardness characteristic similar to the known hardness characteristic of a well-cured restorative material. The disk (10) should preferably be used by being placed on a smooth surface, such as a conventional dental mixing pad. At least one of the openings (16), (17), or (18) is filled with a sample of uncured restorative material, which has a known hardness if properly cured, at a value corresponding to the hardness of the disk material. In practice, a number of different hardness disks will be made available, in thicknesses corresponding to standard restorative depths, such as 2, 3, 4 or 5 mm, etc. The hardness of the disks will vary so that a hardness range is covered, extending over the range of the more readily used commercial restorative materials. The disk (10), filled with restorative material, is then exposed to a conventional source of curing light which is known to be able to properly cure the restorative material. The restorative material should be cured from the cure (top) side (12), in whatever length of time is recommended by the material manufacturer for a restorative thickness corresponding to the thickness of the disk, e.g., corresponding to a 3 mm depth of cure. The material on the bottom side (14) of the disk (10) is then checked to see if it is properly cured using a standard discoid tungsten carbide carver or other instrument, such as a Vhee carver by comparing its hardness to that of the surrounding disk surface contiguous to the filled opening. If the hardness is not relatively close to the hardness of the disk, the material is no longer usable and should be returned to the manufacturer or discarded. The hardness may be compared simply by comparing the carvability of the cured material to the carvability of the surrounding surface of the test disk. The consistency of the carved material should feel equal to or harder than that of the disk material. The disk material hardness should correspond to the hardness of the material when completely cured.

An alternate embodiment is shown in FIG. 4, with the device (10) having a bottom planar surface (20), and a linearly increasing upper surface (22). A plurality of openings (23), (24), (25), (26), and (27) are formed in the body (30) of the device (10), with graduated thicknesses, for example, of between three to eight millimeters. This permits testing for multiple depth cavities. The device (10) would be operated in the exact same way as its counterpart (1) in FIGS. 1-3.

What I claim is:

1. A method for comparative testing of the hardness of a conventional uncured dental composite material following exposure to light energy with a known standard comprising the steps of: filling a sample of said uncured dental composite into an opening extending through a body composed of a polymeric material other than said dental restorative material and having a known hardness, with the sample filling the opening on opposite sides of the body, exposing one side of said body containing said filled sample of uncured dental composite to a source of light energy over a predetermined time frame of standard duration for effecting a cure, and surface scratching or carving said body for comparing the unknown hardness of said sample against the known hardness of said surrounding body, on at least the side of said body opposite the side which was exposed to light energy.

* * * * *